United States Patent [19]

Eini et al.

[11] Patent Number: 5,411,992
[45] Date of Patent: * May 2, 1995

[54] LICE REPELLANT COMPOSITION

[75] Inventors: Meir Eini, Ness Ziona; Dov Tamarkin, Jerusalem, both of Israel

[73] Assignee: Clilco Ltd., Ness Ziona, Israel

[*] Notice: The portion of the term of this patent subsequent to Jul. 13, 2010 has been disclaimed.

[21] Appl. No.: 55,986

[22] Filed: Apr. 29, 1993

Related U.S. Application Data

[63] Continuation of Ser. No. 902,415, Jun. 19, 1992, Pat. No. 5,227,163, which is a continuation of Ser. No. 642,806, Jan. 18, 1991, abandoned.

[51] Int. Cl.$^6$ ..................... A01N 31/08; A01N 65/00
[52] U.S. Cl. ..................... 514/731; 424/195.1; 424/DIG. 10; 514/919
[58] Field of Search ..................... 424/195.1, DIG. 10; 514/731; 564/501

[56] References Cited

U.S. PATENT DOCUMENTS

| | | | |
|---|---|---|---|
| Re. 29,829 | 11/1978 | Bordence | 268/584 |
| 3,626,011 | 12/1971 | Bordenc | 564/501 |
| 4,164,561 | 8/1979 | Hautmann | 424/28 |
| 4,193,986 | 3/1980 | Cox | 424/28 |
| 4,223,161 | 11/1980 | Sato | 252/1 |
| 4,379,168 | 4/1983 | Dotolo | 514/739 |
| 4,405,467 | 9/1985 | Sato | 252/739 |
| 4,466,967 | 8/1985 | Smolanoff | 514/307 |
| 4,536,583 | 8/1985 | Mookherjee | 549/739 |
| 4,587,123 | 5/1986 | Price | 424/195 |
| 4,620,945 | 11/1986 | Mookherjee | 252/522 R |
| 4,663,346 | 9/1987 | Coulston | 424/45 |
| 4,671,960 | 6/1987 | Thielen | 424/195.1 |
| 4,693,890 | 9/1987 | Wilson | 424/78 |
| 4,701,946 | 10/1987 | Apias | 514/65 |
| 4,759,930 | 7/1988 | Granirer | 424/195.1 |
| 4,869,896 | 9/1989 | Coulston | 424/45 |
| 4,886,662 | 12/1989 | Wilson | 424/84 |
| 4,933,371 | 6/1990 | Hink | 514/739 |
| 4,978,677 | 12/1990 | Gehret | 514/450 |
| 5,227,163 | 7/1993 | Eini et al. | 424/195.1 |

FOREIGN PATENT DOCUMENTS

| | | |
|---|---|---|
| 1230826 | 9/1983 | Canada . |
| 0433132 | 5/1990 | European Pat. Off. . |
| 1175895 | 6/1957 | France . |
| 2371190 | 11/1976 | France . |
| 2447681 | 1/1979 | France . |
| 2622103 | 10/1987 | France . |
| 2866691 | 6/1978 | Germany . |
| 89/06904 | 1/1989 | WIPO . |
| 90/00859 | 7/1989 | WIPO . |
| 90/09738 | 2/1990 | WIPO . |
| 91/08670 | 12/1990 | WIPO . |
| 91/15118 | 3/1991 | WIPO . |

OTHER PUBLICATIONS

Drescher, R., "Insecticidal Preparations for Rooms", Ger. Offen. 2,318,413, Chemical Abstracts, filed Apr. 12, 1973, Chemical Abstracts, vol. 082, No. 17, Sec. 005, Abstract No. 107569.

Mikasa Chemical Industrial Co., Ltd., "Compositions Containing Ketone Derivatives, Eucalyptus, and Its Extract, Insecticide and Adhesives for Cockroach Control", Japan Kohai Tokkyo Koho JP 62,114,904, filed Nov. 13, 1985, Chemical Abstracts, vol. 112, No. 07, Sec. 105, Abstract No. 050625.

Trop, Sci., vol. 25, Iss. 4, pp. 249–252, 1985.

Kamru, "Plantes Medicinales et Phyto Therape," Tome XVI, p. 34 (1982).

Hwang, et al., J. Chem. Ecol., vol. 11, p. 1297 (1985).

Ruledge, J. Am. Mosquito Control Assoc., vol. 4, p. 414 (1988).

*Primary Examiner*—John W. Rollins
*Attorney, Agent, or Firm*—Mark M. Friedman

[57] ABSTRACT

It has been discovered that terpenoids, especially terpenoid-alcohols (terpene-ols) and terpenoid-esters, and some aldehydes and ketones of terpenes, in a concentration of between 0.01% and 50% by weight, most preferably between 0.01% and 10%, are very good lice repellents. The active agent can be combined with a pharmaceutically and/or cosmetically acceptable carrier for topical administration, such as an aqueous or alcohol solution, a gel, cream, or a powder, and administered with or without additives such as other insect repellents, agents increasing solubility or delaying release of active agents, antimicrobials, antioxidants and fragrances. Examples demonstrate efficacy in in vitro and in in vivo testing.

15 Claims, 2 Drawing Sheets

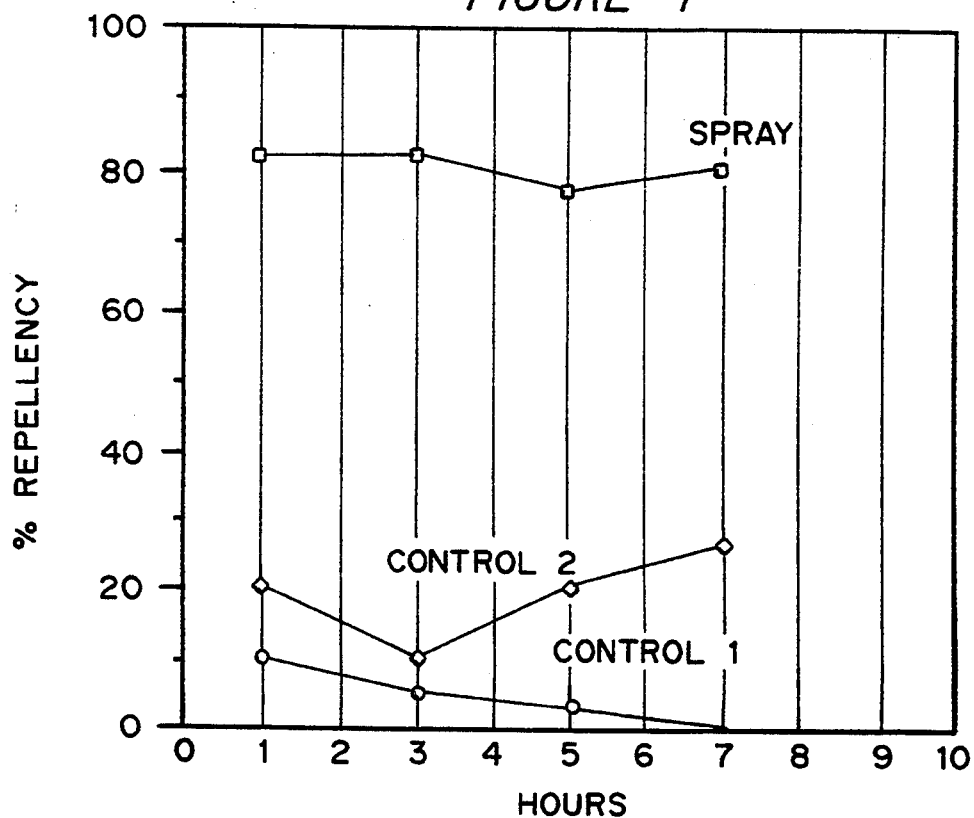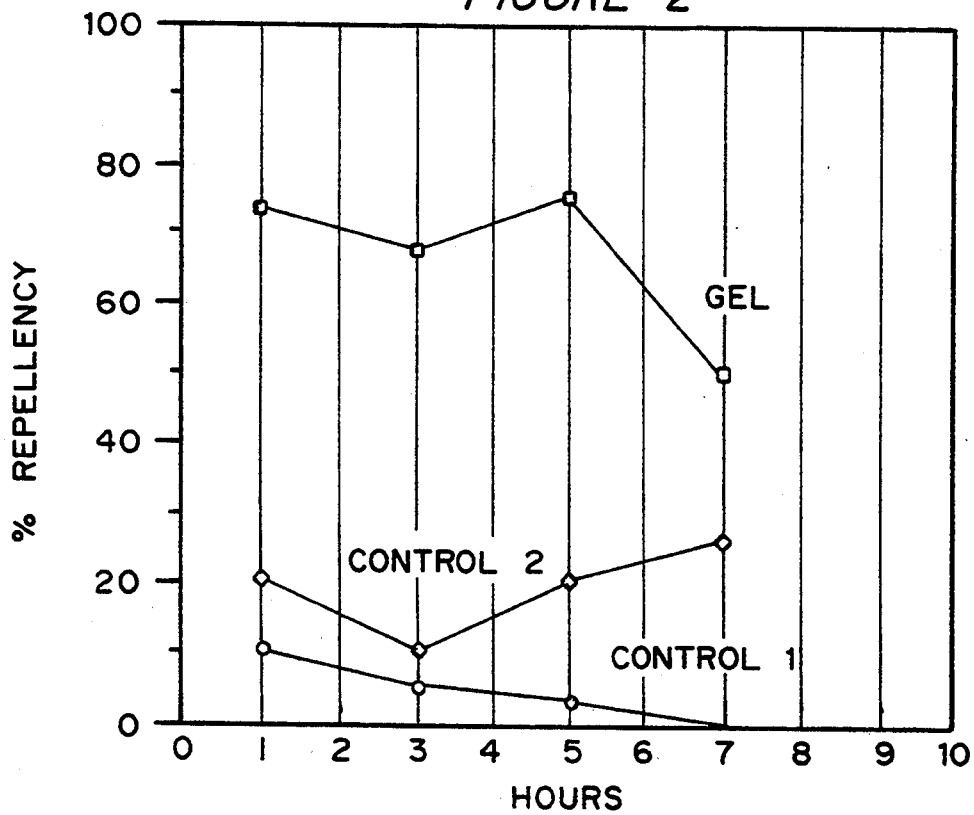

5,411,992

LICE REPELLANT COMPOSITION

This is a continuation of U.S. Ser. No. 07/902,415 filed Jun. 19, 1992, now U.S. Pat. No. 5,227,163, which is a continuation of U.S. Ser. No. 07/642,806 filed Jan. 18, 1991, now abandoned.

BACKGROUND OF THE INVENTION

Lice are a common pest which are widely distributed throughout the world and infest both humans and animals. They are spread by contact and are a problem even under relatively sanitary conditions.

Lice are insects about two to three millimeters in length. They lay eggs called nits, which look like white grains of sand and are firmly attached to the hairs by a cementlike excretion. The eggs generally hatch in about eight to ten days at body temperature.

The common latin name for the whole family is "Anoplura". Human lice are divided into two genera: Head lice, *Pediculus capitis* or *Pediculus humanus capitis*, and Body lice or Clothing lice, *Pediculus humanus humanus* or *Pediculus corporis*; and Pubic lice, *Phthirius pubis*. Lice are spread by crowding and common usage of clothing and combs. Initially, infestations result at most in irritation, which can lead to infection of the irritated area, although there are at least three major diseases that are primarily transmitted by lice: epidemic typhus, trench fever and relapsing fever.

Lice on animals such as the dog are commonly associated with itching and are found under matted fur and around the ears, head, neck and shoulders. There are two types of lice, biting lice that feed on skin scales and sucking lice that feed on the dog's blood and can cause a severe anemia.

Special combs are used to remove the eggs from the hair. Lice are usually treated by application of an insecticidal product, such as 0.1 to 2% pyrethroids with synergists, 68% benzyl benzoate, 6% DDT, 12% benzolaine and 14% Tween™ 80, diluted 1:5. Several insecticides have also been used for treatment of body lice, including 10% DDT, 1% lindane, and pyrethrum powders. Animals are treated with the insecticide three to four times at ten day intervals, along with cleaning or disposal of associated bedding. It would clearly be preferable to have a treatment which prevents infestation, rather than a treatment after infestation of either a person or an animal. Although a number of insect repellents have been developed, most are relatively specific to a particular type of insect, such as mosquitos, or smell bad, which would limit usefulness under routine conditions, as in a school for young children. Compounds that have been used for control of insects such as mosquitos include DEET (diethyl toluamide) and some terpenoids, as reported by Hwang, et al, *J. Chem. Ecol.*, 11, 1297 (1985); and Ruledge, *J. Am. Mosquito Control Assoc.* 4, 414 (1988). In the work reported by Hwang, et al., a screen done on terpenoids as mosquito repellent indicated that terpenoids are effective repellents. Ruledge notes that α-terpineol is useful in mosquito repellent. U.S. Pat. Re. No. 29,829 to Bordenca, et al., discloses that lower hydroxyalkyl amines in which at least one of the amino hydrogens is replaced by an acyclic monoterpenyl radical or hydrogenated acyclic monoterpenyl radical are useful insect repellents. U.S. Pat. No. 4,193,986 to Cox, U.S. Pat. No. 4,759,930 to Granirer, et al., U.S. Pat. No. 4,671,960 to Thielen, et al., and U.S. Pat. No. 4,587,123 to Price claim that eucalyptus oil is an effective flea repellant.

None of these repellents is specific for lice nor proven to be efficacious.

It is therefore an object of the present invention to provide repellents for lice that are safe, efficacious, pleasant smelling, and relatively inexpensive, but which do not contain toxic insecticides.

It is another object of the present invention to provide such repellents that are effective in a variety of carriers, including hair sprays, shampoos, and powders.

It is still another object of the present invention to provide such repellents that are effective in repelling both human and animal lice.

SUMMARY OF THE INVENTION

It has been discovered that terpenoids, especially terpenoid-alcohols (terpene-ols) and terpenoid-esters, and some aldehydes and ketones of terpenes, in a concentration of between 0.01% and 50%, most preferably between 0.01% and 10%, are very good lice repellents. Most perfumes and a number of essential oils containing a high content of terpene-ols and esters, greater than 40%, are also very good lice repellents, including bergamot, sage, styrax, peppermint, and pine siberian.

The active agent can be combined with a pharmaceutically and/or cosmetically acceptable carrier for topical administration, such as an aqueous or alcohol solution, a gel, cream, or a powder, and administered with or without additives such as other insect repellents, agents increasing solubility or delaying release of active agents, antimicrobial preservatives, antioxidants and fragrances. A number of agents for delaying release of substances have been developed, including biodegradable natural or synthetic polymeric microparticles (including microspheres and microcapsules), liposomes, cyclodextrins, various surfactants, and polymers decreasing the volatility of the terpenes.

Examples demonstrate efficacy in in vitro and in in vivo testing.

BRIEF DESCRIPTION OF THE DRAWINGS

FIG. 1 is a graph of the time dependent repellency of LICE-FREE-SPRAY of example 3, plotting % repellency against hours.

FIG. 2 is a graph of the time dependent repellency of LICE-FREE-GEL of example 3, plotting % repellency against hours.

DETAILED DESCRIPTION OF THE INVENTION

Figure 3:
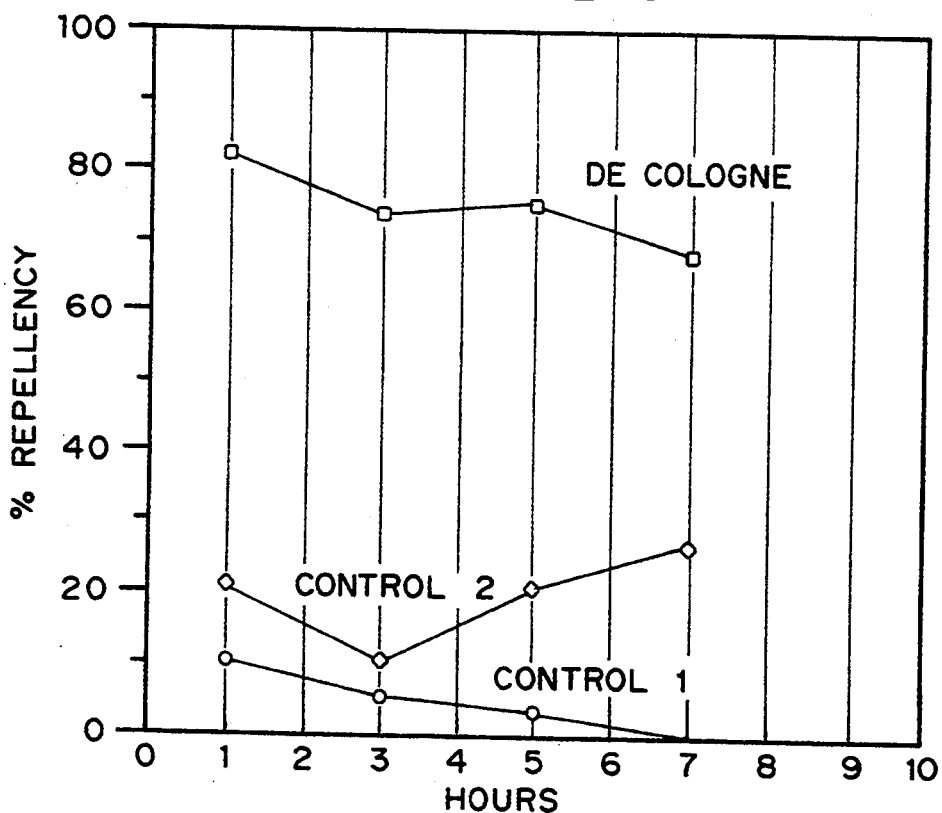
FIG. 3 is a graph of the time dependent repellency of LICE-FREE-DE COLOGNE of example 3, plotting % repellency against hours.

The present invention is based on the discovery that terpenes, topically applied to the hair and skin, will effectively repel lice. Certain classes of the terpenes are more effective and therefore commercially useful. Effective concentrations are low enough that the preparations are not unpleasant in their smell or appearance. An effective amount of terpene or terpenes can also be combined with a number of aqueous and non-aqueous formulations and still be effective.

Terpenes are well known naturally occurring unsaturated hydrocarbons ($C_{10}H_{16}$) found in many essential oils and oleophilic plant resins. As used herein, "terpene" includes the saturated derivatives of the unsaturated hydrocarbons as well as mixtures of terpenes. "Terpenoids" includes terpenes and terpenes having a functional group, such as a hydroxy, aldehyde, ketone, or ester.

The carbon backbone of terpenes are formed exclusively of head to tail dimerization products of isopentyl (isoprene) units. There are three principal monoterpene hydrocarbon backbones:

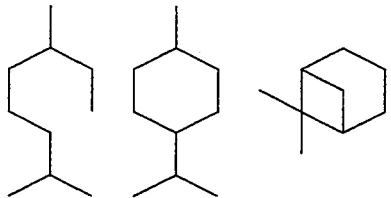

Many of these compounds are commercially available. Methods for synthesis of others are also known to those skilled in the art. Examples of references books containing methods of synthesis include *Chemistry of Terpenes and Terpenoids*, A. A. Newman, ed., (Academic Press, London and New York, 1972), and references cited therein, the teachings of which are incorporated therein.

Terpenoid-alcohol or Terpene-ols are terpenoids which have at least one hydroxyl group. Examples of terpene-ols include: $C_{10}H_{16}O$ compounds, perillyl alcohol, carveol, myrtenol, and cis-verbenol; $C_{10}H_{18}O$ compounds, myrtanol, iso-pinocampheol, dihydrocarveol, isopulegol, terpineol, terpinen-4-ol, nerol, geraniol, and linalool, and $C_{10}H_{20}O$ compounds, menthol, β-citronellol, and dihydro-myrcenol.

Terpenoid-esters are terpenoids which have at least one ester group which is the product of the bonding of the hydroxyl group of a terpene-ol with an aliphatic carboxylic acid that can contain functional groups such as the hydroxyl or amine on the aliphatic chain. Examples of suitable aliphatic carboxylic acids include acetic acid, propionic acid, lactic acid, and various amino acids. Examples of terpenoid-esters include: carvyl acetate, carvyl propionate, and menthyl lactate.

The most potent group of repellents are the terpene-ols. Esters of terpene-ols are potent, as well. Essential oils which contain terpenoids and perfumes which contain terpenoids are also useful. Examples of essential oils which have high content of terpene-ols and esters: Bergamot (62%); Sage (>50%); styrax (>50%); Peppermint (>50%); Pine Siberian (75%). Terpenes, aldehydes and ketones vary in their usefulness but as a general group have potential as lice-repellent.

Any concentration above 0.01% will repel lice. The preparations tested in vivo (including clinical trials) contained 0.1-5% by weight, and were found to be effective. Since high concentrations of the terpenoids have very strong odors, concentrations above 50% are not useful. Good protection can be obtained in the range of 0.01-50%, most preferably between 0.1 and 10% by weight.

The following groups of additives can be incorporated in a lice repelling preparation in addition to the terpenoids:

a. Other insect repellents, such as dimethyl phthalate and DEET (dimethyl-toluamide).
b. Materials which can improve the effect of the terpenoids, for example, low molecular weight alcohols, which enhance volatility of the terpenoids.
c. Release and controlled delivery materials which can prolong the time of action, for example by way of microencapsulation which results in slow release. Additives of this nature include various surfactants. A number of agents for delaying release of substances have been developed, including biodegradable natural or synthetic polymeric microparticles (including microspheres and microcapsules), liposomes, cyclodextrins, various surfactants, and polymers decreasing the volatility of the terpenes.
d. Formulation materials, which include solvents, surfactants, antimicrobial preservatives, antioxidants and fragrance materials.

The active ingredients can be incorporated in any kind of topical preparation, such as a spray, liquid, gel, cream, shampoo, conditioner, or mousse. Several examples are provided. Many additional preparations are known to those skilled in the art or commercially available.

Four methods were employed in order to determine the efficacy of active substances and finished products: three laboratory tests and one field trial. The procedures are described below in the following non-limiting examples. It is important to emphasize that the three laboratory methods are different in procedures and conditions and hence differ in their absolute results. As a rule, method 1 is more facile and gives more reproducible results versus method 3 and thus is preferable as a quality control bioassay.

Example 1

Screening of Compounds for in Vitro Lice-Repellency

Screening tests were performed on many substances of the following groups: terpenes (hydrocarbons), terpenoid alcohols, terpenoid esters, terpenoid aldehydes and ketones, essential oils which contain terpenoids and perfumes which contain terpenoids, as well as various general insect repellents, for lice-repellency. Each experiment included exposure of the lice to different concentrations of the tested substance, and measuring the dose response of those materials.

Standard in vitro Test on Filter Paper

A petri-dish method was used to examine the repellency of the solutions for lice. A filter paper (Whatman No. 4, 5.5 cm in diameter) was secured in a petri-dish. A 100 μl portion of the test solution was placed on a corduroy patch (1.5 cm²). The material was allowed to dry for 30 min. at room temperature (20°±3° C.) and the patch was placed at the periphery of the petri-dish. A patch treated with a control solution (96% Ethanol) was placed on the opposite side of the dish. Twenty female lice which had been fed 24 hours previously were placed in the middle of the dish. A box was placed over the dish and it was covered with a dark cloth in order to keep the test area in the dark. The experiment was carried out at room temperature (20°±3° C.) and lasted 10 min. The number of lice on the treated and controlled patches as well as on the area between the patches was recorded in a protocol. The experiment was repeated three times for each sample.

% repellency was calculated by the following formula:

% REPELLENCY = (1 − T/C) × 100 where:
T = number of lice on the treated patch
C = number of lice on the untreated patch
The following terms were recorded:
$RC_{80}$ = Concentration giving 80% repellency.
$RC_{50}$ = Concentration giving 50% repellency.
$RD_{80}$ = mg/cm² giving 80% repellency.
$RD_{50}$ = mg/cm² giving 50% repellency.
The results are summarized as follows:

Terpenes: Five terpenes, as shown in Table 1, were tested. They are moderate repellents. Typical RC-80 is 1–4% and typical RD-80 1–3 mg/cm².

Terpenoid-alcohols ("Terpene-ols"): Sixteen terpene-ols, as shown in Table 1, were tested. They all repel lice. They are good to excellent repellents, having typical RC-80 values between 0.02–1, and typical RD-80 of 0.01–1.

Terpenoid-esters: Four esters were tested. All of them are good repellents, having RC-80 values between 0.1–0.8, and RD-80 values between 0.07–0.5.

Terpenoid-aldehyde and ketones: Seven of these were tested. They all repel lice, but the range of activity is wide: some are very good and some are poor (see Table 1).

Essential oils which contain terpenoids and perfumes which contain terpenoids: Ten essential oils were tested with lice, and in parallel were analyzed by GC-Mass Spectrography. Eight of the oils contain terpene-ols in high concentration (more than 40%). Those which contain terpene-ols are good repellents having RC-80 values between 0.7–1.5, and RD-80 values between 0.5–1.

The results for terpene-ols, terpene-esters, other terpenoids and essential oils which contain terpenoids are shown in Table 1.

TABLE 1

| RC and RD Values of Terpenoids | | | | | |
|---|---|---|---|---|---|
| TYPE OF COMPOUND | NAME OF COMPOUND | $RC_{80}$ (%) | $RD_{80}$ mg/cm² | $RC_{50}$ (%) | $RD_{50}$ mg/cm² |
| TERPENE-OL | CARVEOL | 1.500 | 1.050 | 0.600 | 0.420 |
| | PERILLIL ALCOHOL | 0.030 | 0.020 | 0.010 | 0.007 |
| | Cis VERBENOL | 2.000 | 1.400 | 1.000 | 0.700 |
| | MYRTENOL | 0.900 | 0.630 | 0.500 | 0.350 |
| | DIHYDRO CARVEOL | 0.900 | 0.630 | 0.400 | 0.280 |
| | ISOPULEGOL | 0.800 | 0.560 | 0.500 | 0.350 |
| | Cis MYRTANOL | 1.000 | 0.700 | 0.600 | 0.420 |
| | NEROL | 0.800 | 0.560 | 0.500 | 0.350 |
| | β-CITRO-NELLOL | 0.070 | 0.049 | 0.020 | 0.014 |
| | α-TERPINEOL | 0.080 | 0.056 | 0.040 | 0.028 |
| | GERANIOL | 0.020 | 0.014 | 0.005 | 0.004 |
| | LINALOOL | 0.080 | 0.056 | 0.020 | 0.014 |
| | MENTHOL | 0.150 | 0.105 | 0.030 | 0.021 |
| | DIHYDRO MYRCENOL | 0.800 | 0.560 | 0.600 | 0.420 |
| | ISOPINO-CAMPHEOL | 0.300 | 0.210 | 0.200 | 0.140 |
| | TERPINEN-4-OL | 0.090 | 0.063 | 0.020 | 0.014 |
| TERPENE-ESTER | MENTHYL LACTATE | 0.100 | 0.070 | 0.050 | 0.035 |
| | CARVYL PROPRIONATE | 0.600 | 0.420 | 0.200 | 0.140 |
| | ISO BORNYL ACETATE | 0.800 | 0.560 | 0.600 | 0.420 |
| | DIHYDRO-CARVYL ACETATE | 0.300 | 0.210 | 0.150 | 0.105 |
| TERPENE | β PINENE | 1.100 | 0.770 | 0.200 | 0.140 |
| | α TERPINENE | 1.500 | 1.050 | 0.900 | 0.630 |
| | CARENE | 2.000 | 1.400 | 1.000 | 0.700 |
| | + LIMONENE | 3.000 | 2.100 | 2.000 | 1.400 |
| | − LIMONENE | 4.000 | 2.800 | 3.000 | 2.100 |
| ESSENTIAL OIL | BERGAMOT | 0.700 | 0.490 | 0.200 | 0.140 |
| | CLAY SAGE | 0.800 | 0.560 | 0.200 | 0.140 |
| | STYRAX | 0.200 | 0.140 | 0.100 | 0.070 |
| | PEPPERMINT | 1.000 | 0.700 | 0.300 | 0.210 |
| | PINE SIBERIAN | 1.500 | 1.050 | 0.900 | 0.630 |
| ALDEHYDE & KETONE | CITRAL | 0.600 | 0.420 | 0.300 | 0.210 |
| | IONONE | 0.600 | 0.420 | 0.250 | 0.170 |
| | DIHYDRO CARVONE | 0.500 | 0.350 | 0.200 | 0.140 |
| | PULEGONE | 0.700 | 0.490 | 0.400 | 0.280 |

RC = Repellency concentration = (1 − T/C) × 100
T = Number of lice on the treated patch
C = Number of lice on the untreated patch
RD = Repellency dosage in mg/cm²
$RC_{80}$ = Concentration giving 80% repellency
$RC_{50}$ = Concentration giving 50% repellency
$RD_{80}$ = mg/cm² giving 80% repellency
$RD_{50}$ = mg/cm² giving 50% repellency These results lead to the following conclusions:
1. The most potent group of repellents are the terpene-ols.
2. Esters of terpene-ols are potent as well.
3. Essential oils which contain terpenoids and perfumes which contain terpenoids are also useful. Examples of essential oils which have high content of terpene-ols and esters: Bergamot (62%); Sage (>50%); Styrax (>50%); Peppermint (>50%); Pine Siberian (75%).
4. Aldehydes and ketones of terpenes vary in their usefulness but as a general group have potential as lice-repellents.

Any concentration above 0.01% will repel lice.

Example 2:

In Vitro Testing of Lice Repellency on Hair to Compare Effectiveness Against Body and Head Lice A bundle of human hair (10 cm long) were dipped into the repellent solution, containing 52% purified water, 44% alcohol, 2% terpineol and 2% peppermint oil, until it was half way immersed and held there for five seconds. The hairs were then dried for one hour at room temperature. The ends of the hairs were held in position on double sided sticky tape on a petri dish. Ten lice were placed in the center of the hairs between the treated and untreated areas. This was done in a dark room and the direction of movement of the lice was followed with the aid of an infra-red lamp, and recorded in a protocol. The experiment was repeated three times for each sample.

The results were as follows:

| | Treated area | Untreated area |
|---|---|---|
| Head lice (mean value) | 3 | 7 |
| Body lice (mean value) | 3.5 | 7.5 |

It was concluded on the basis of these results that head lice and body lice are similarly repelled by the product.

Example 3:

In Vivo Test of Lice Repellency on Rabbits

Body lice were reared in the laboratory by feeding them every 48 hours on rabbits. Lice were placed on the shaved abdomen of a white rabbit and left until they fed to satiety. Outside the host the lice were maintained at a temperature of 30°±1° C., and relative humidity of 70±10%

The abdomen of a New Zealand white rabbit was shaved and 100 μl of the test substance was evenly distributed over an area 2.5×5 cm. A glass cylinder 5 cm high with an internal diameter of 3.5 cm was placed on the rabbit's abdomen so that one half of it was covering the treated area and the other half the adjacent untreated area. 40 human body lice (*Pediculus humanus humanus*) (20 adults and 20 nymphs) which had been fed 24 hours previously were placed in the middle of the cylinder between the treated and untreated area, and the cylinder was covered with a dark cloth in order to keep the test area in the dark. The lice remained on the body of the rabbit for 5 minutes during which time over 95% of them had started feeding. The number of lice found on the treated area was then recorded and the specimen was photographed. Room temperature during the test was 20°±3° C. For comparison to the tested samples, two controls were also tested: 70% Ethanol (Frutarom, C. P.) and 33% Dimethyl Phthalate (in 70% Ethanol).

The products were topically applied as a spray, lotion or gel on human hair and skin, to repel lice. The above procedure was carried out 1, 3, 5, and 24 hours after application of a test substance. Each substance was tested three times on three different rabbits on three different occasions.

The results of the experiments, expressed in percents of efficacy, summarized in Tables 2 and 3, indicate highly effective repellency of the three products that were tested for at least 5-7 hours.

The results confirm the in vitro studies, demonstrating the products' efficacy on a living body, under conditions close to those which prevail in humans (skin temperature, humidity, existence of hair and availability of blood favored by lice). New Zealand white rabbits have these properties, and they are often used to simulate behavior of lice on humans.

Results

The results of the examinations are presented in Tables 2 and 3, and in FIGS. 1 to 3. FIG. 1 is a graph of the time dependent repellency of LICE-FREE-SPRAY. FIG. 2 is a graph of the time dependent repellency of LICE-FREE-GEL. FIG. 3 is a graph of the time dependent repellency of LICE-FREE-DE COLOGNE.

The products tested were:

LICE-FREE SPRAY contains: 50% purified water, 42% alcohol, 2% diethyltoluamide, 2% diethylphthalate, 2% terpineol and 2% styrax oil.

LICE-FREE GEL contains 46.6% purified water, 45% alcohol, 2% diethyl toluamide, 2% methyl lactate, 2% menthol, 0.9% Carbomer ™ 940, and 1.5% Triethanolamin.

LICE-FREE-DE-COLOGNE contains: 50% purified water, 44% alcohol, 2% citronellol, 2% carvyl acetate and 2% bergamot oil.

TABLE 2

Number of Lice (Out of 40) Found in the Treated Area (results are presented in triplicate)

| Product | | Time (hours) | | | | |
|---|---|---|---|---|---|---|
| | | 1 | 3 | 5 | 7 | 24 |
| LICE-FREE - SPRAY | (a) | 1 | 1 | 4 | 3 | 19 |
| | (b) | 5 | 4 | 4 | 4 | 14 |
| | (c) | 6 | 6 | 6 | 5 | 21 |
| LICE-FREE GEL | (a) | 3 | 5 | 4 | 9 | 21 |
| | (b) | 5 | 8 | 3 | 10 | 19 |
| | (c) | 8 | 7 | 8 | 10 | 19 |
| LICE-FREE-DE COLOGNE | (a) | 3 | 5 | 4 | 7 | 18 |
| | (b) | 1 | 6 | 4 | 6 | 21 |
| | (c) | 7 | 5 | 7 | 5 | 20 |
| Control 1 - 70% Ethanol | (a) | 18 | 16 | 17 | 17 | N.D. |
| | (b) | 18 | 20 | 22 | 25 | N.D. |
| | (c) | 18 | 21 | 19 | 18 | N.D. |
| Control 2 - 33% D.M.P. | (a) | 21 | 16 | 16 | 18 | N.D. |
| | (b) | 12 | 18 | 14 | 14 | N.D. |
| | (c) | 15 | 20 | 18 | 12 | N.D. |

(a) - First experiment
(b) - Second experiment
(c) - Third experiment
N.D. - Not Determined
D.M.P. - Dimethyl Phthalate
% Repellency was calculated according to equation 1.

Equation 1 - % Repellency = $\frac{1/2 A - n}{1/2 A} \times 100$

Where:
A = Total Number of lice
n = Mean number of lice found in the treated area
$n = \frac{n_a + n_b + n_c}{3}$ According to Equation 1, when lice are evenly distributed between the treated and untreated areas ($n = \frac{1}{2} A$), % Repellency=0, and when no lice are left in the treated area (n=0), % Repellency=100.

The mean % Repellency values, calculated for LICE-FREE products are presented in Table 3 and FIGS. 1-3.

TABLE 3

% Repellency of "LICE-FREE" products (Mean Values)

| Product | % Repellency | | | |
|---|---|---|---|---|
| | 1 | 3 | 5 | 7 |
| LICE-FREE SPRAY | 80 | 82 | 77 | 80 |
| LICE FREE GEL | 73 | 67 | 75 | 50 |
| LICE-FREE DE COLOGNE | 82 | 73 | 75 | 68 |
| Control 1 (70% Ethanol) | 10 | 5 | 3 | 0 |
| Control 2 (Dimethyl Phthalate) | 20 | 10 | 20 | 26 |

The time dependant repellency of the three products is presented in FIGS. 1-3.

Treatment with LICE-FREE-SPRAY resulted in 77-82% repellency against lice for a duration of at least 7 hours.

Treatment with LICE-FREE-GEL resulted in 67-75% repellency against lice for a duration of at least 5 hours.

Treatment with LICE-FREE-DE COLOGNE resulted in 68-82% repellency against lice for a duration of at least 7 hours.

For comparison, the insect repellent, Dimethyl Phthalate gave poor results (10-25% repellency) and in the control of 70% Ethanol no repellency was found.

On the basis of this study it can be concluded that the three products, LICE-FREE SPRAY, LICE-FREE GEL and LICE-FREE-DE COLOGNE are effective as lice repellents for at least 5-7 hours.

Example 4:

Demonstration of Efficacy of Lice-Repellant Shampoo and Conditioner.

The efficacy of a shampoo and a hair-conditioner, aimed at repellency of human lice was examined in an in vivo procedure on rabbits. Each experiment included a terpenoid containing product and four controls: 70% Ethanol, Dimethyl phthalate, placebo shampoo and placebo conditioner. All experiments were repeated three times, and the results were consistent, as shown by Table 4.

The following products were tested:

SHAMPOO contains 56.15%, purified water, 12% TEA Lauryl, Sulphate (40%), 14% Cocamphoglycinate (and) Sodium Trideceth Sulphate (35%), 8%.Sodium laureth sulphate (27%), 2% Lauramide DEA (85%), 2% Terpinen-4-ol, 2% α-Terpineol, 2% Perillyl alcohol, 1% Glycol Monostearate, 0.4% Citric Acid, 0.25% Fragrance, 0.2% Preservatives.

CONDITIONER contains 79.8% purified water, 7% protein hydrolysate, 6% Cetrimonium chloride (25%), 1.5% Vitamin F, 2.8% PEG-150 Stearate, 2% Diethyl Toluamide, 2% Terpineol, 2% Geraniol, 0.5% Cetyl Alcohol, 0.2% Preservatives, 0.2% Fragrance.

TABLE 4

Number of Lice (Out of 40) Found in the Treated Area

| Product | Time (hours) | | | |
|---|---|---|---|---|
| | 1 | 3 | 4 | 7 |
| LICE-FREE - SHAMPOO | 5 | 7 | 8 | 10 |
| | 8 | 8 | 10 | 11 |
| | 5 | 8 | 7 | 10 |
| LICE-FREE - CONDITIONER | 7 | 10 | 11 | 12 |
| | 8 | 8 | 9 | 12 |
| | 9 | 9 | 10 | 12 |
| Control 1 - 70% Ethanol | 10 | 20 | 19 | 22 |
| | 19 | 22 | 22 | 26 |
| | 20 | 18 | 22 | 24 |
| Control 2 - 33% D.M.P. | 21 | 16 | 16 | 18 |
| | 12 | 18 | 14 | 14 |
| | 15 | 20 | 18 | 12 |
| Control 3 - PLACEBO SHAMPOO | 15 | 17 | 19 | 22 |
| | 16 | 18 | 20 | 22 |
| | 16 | 22 | 20 | 21 |
| Control 4 - PLACEBO CONDITIONER | 16 | 18 | 19 | 21 |
| | 17 | 18 | 22 | 22 |
| | 16 | 20 | 20 | 23 |

D.M.P. - Dimethyl Phthalate
% Repellency was calculated according to equation 1.

Equation 1: % Repellency = $\frac{1/2 A - n}{1/2 A} \times 100$

Where:
A = Total Number of lice
n = Mean number of lice found in the treated area
$n = \frac{n_a + n_b + n_c}{3}$ According to Equation 1, when lice are evenly distributed between the treated and untreated areas (n=½ A), % Repellency=0, and when no lice are left in the treated area (n=0), % Repellency=100.

The mean % Repellency values are presented in Table 5.

TABLE 5

% Repellency of "LICE-FREE" products (Mean Values)

| Product | % Repellency After Time (hours) | | | |
|---|---|---|---|---|
| | 1 | 3 | 5 | 7 |
| LICE-FREE SHAMPOO | 70 | 62 | 58 | 48 |
| LICE-FREE CONDITIONER | 60 | 55 | 50 | 40 |
| Control 1 (70% Ethanol) | 5 | 3 | 2 | 0 |
| Control 2 (Dimethyl Phthalate) | 20 | 10 | 20 | 26 |

TABLE 5-continued

% Repellency of "LICE-FREE" products (Mean Values)

| Product | % Repellency After Time (hours) | | | |
|---|---|---|---|---|
| | 1 | 3 | 5 | 7 |
| Control 3 (Placebo Shampoo) | 22 | 8 | 2 | 0 |
| Control 4 (Placebo Conditioner) | 18 | 7 | 2 | 0 |

Figure 4:
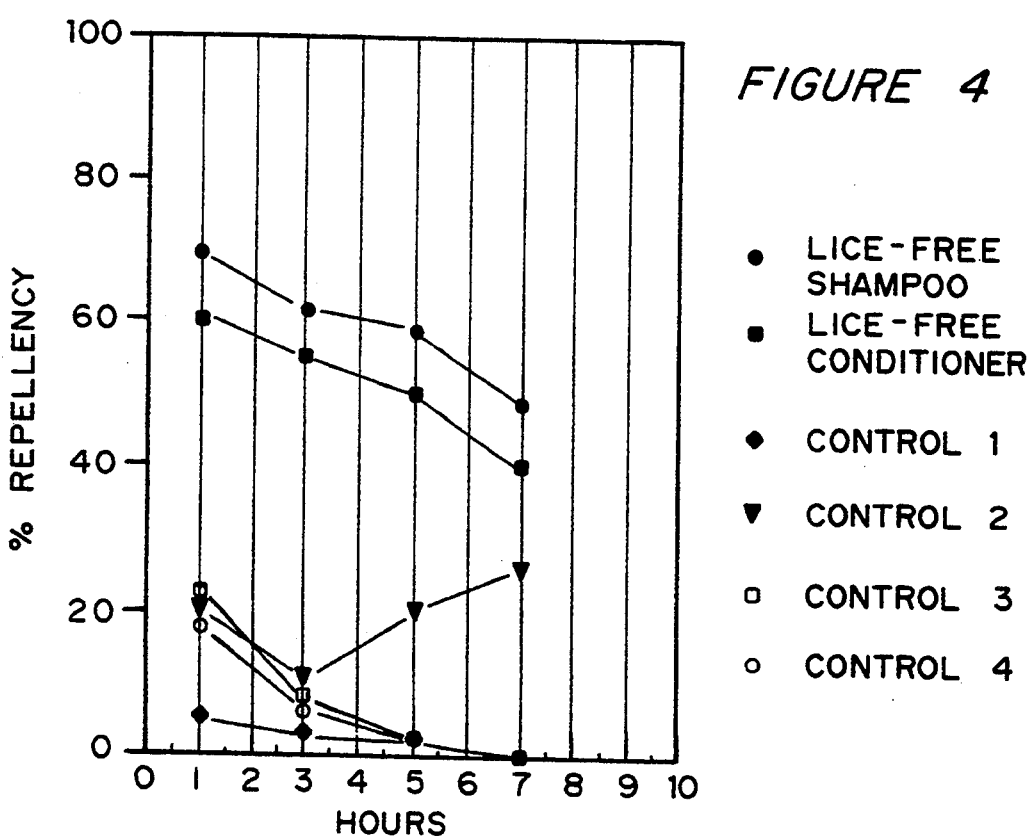
FIG. 4 is a graph of the % repellency over time (hours) of the lice-repellent shampoo and lice-repellent conditioner of example 4, as compared with controls not containing terpenes.

FIG. 4 is a graph of the % repellency over time (hours) of the lice-repellent shampoo and lice-repellent conditioner, as compared with controls not containing terpenes.

The results indicate moderate to high effectiveness lasting for 3 to 5 hours. The duration of effectiveness of the shampoo and conditioner were shorter than the duration of the spray.

Example 5:

Field Trial Testing of Effectiveness of Lice repellency on School Age Children.

The product "Lice Free", intended for the prevention of lice infestation, containing 50% purified water, 42% alcohol, 2% Diethyl Toluamide, 2% Diethyl Phthalate, 2% Terpineol, and 2% Styrax essential oil, was examined in a controlled field study. This study, after receiving the authorization of the Helsinki Committee, was conducted by the Kaplan Hospital, Pediatric Department A, under the leadership of Prof. Y. Barak. After receiving the consent of the children's parents, the children were diagnosed according to their state of pediculosis.

In order to carry out this study, a group of one hundred twenty nine children were selected who met the criteria detailed in the study protocol. The study was carried out at two sites: Kibbutz Masu'to Itzhak, performed by nurse Rivka Nadivi, and in Zefat, performed by nurse Raya Sho'an. The participants were divided into a "test group" and a "control group". The Test group consisted of sixty two children and the control group consisted of sixty seven children.

The results of this trial indicated that the probability of lice infestation in a child is 14.9 times greater if the product is not applied. This means the product gives excellent protection against lice infestation.

Materials and Methods

The test product, containing 50% purified water, 42% alcohol, 2% Diethyl Toluamide, 2% diethyl phthalate, 2% Terpineol, and 2% Styrax essential oil, was provided to the nurses. The product is presented in a spray bottle, equipped with a nozzle of 0.10 ml. The control product, containing 50% purified water and 50% alcohol, was provided in bottles similar to the test product. According to the protocol, the users were instructed to spray four to eight spray strokes (0.40-0.80 ml), twice a day (morning and noon) on a child's hair, and then distribute the product by hand or by a regular hair brush throughout the hair.

Definitions, Postulates and Instructions

The following definitions, postulates, and instructions were made:

Pediculosis—A state in which a person bears lice or lice eggs on his head.

Low state of infestation—Less than 10% of the population have pediculosis.

Medium state of infestation—10–20% of the population have pediculosis.

High state of infestation—Above 20% have pediculosis.

Protection factor—A number expressing the ratio between the rates of infestation in the untreated group vs. the treated group.

$$\text{PROTECTION FACTOR} = \frac{\text{No. of infested untreated objects/Total No. of untreated.}}{\text{No. of infested treated objects/Total No. of treated.}}$$

As per the advice of Dr. K. Mumcuoglu of the Hebrew University Medical School, Department of Parasitology, the implication of the value of the protection factor is as follows:

1 means "No Protection";
3 means "Low–Medium Protection" (reducing the probability of infestation three times);
5 means "High Protection" (reducing the probability of infestation five times); and
7 more means "Excellent Protection".

For example, a protection factor of 6 indicates a state in which the probability of lice infestation in a child is six times greater without applying the product.

According to the information received from the Ministry of Health, the average national affliction rate in Israel is 15–20%. The main afflicted population included children between the ages of two and twelve. In an average Israeli home a child is examined weekly or biweekly and is treated based on his/her needs.

The population for a given study included only children of a set age range (±2 years). During the period of study, no other lice product was used by the participants. Children having any scalp diseases were not allowed to participate. The study took place in groups having a medium-high state of infestation.

The following details were recorded for each participant: age, gender, weight, height, number of siblings, color of hair, length of hair. In order to avoid participants who have individual immunity to lice infestation, the study excluded children who reported that they had never had lice.

All participants were examined for the state of pediculosis. The diagnosis prior to and after the study were handled by the same personnel. Children already infested by lice and/or eggs and children with any type of scalp disease were not treated. Children without lice and/or eggs received numbered bottles of the product (test or control) in a randomized manner. Each child was treated twice a day, five to six hours apart, according to instructions on the bottle: "Spray four to eight spray strokes on hair and comb with a regular comb". Each participant was checked again at the end of the study and the status of his/her pediculosis noted. If irritation occurred, as per each child's answers to questions, it was also noted.

Characteristics of Participants

Test Group: Total 62 Children:
13 (20.7%) boys;
49 (79.3%) girls
33 (53.2%) aged 2–5 years;
23 (37.1%) aged 6–9 years
6 (9.7%) aged 10–13 years;
15 (24.2%) have fair hair;
47 (75.8%) have dark hair;
37 (59.7%) have short hair;
25 (40.3%) have long hair Control Group: Total 67 Children
44 (65.7%) boys;
23 (34.3%) girls
43 (64.2%) aged 2–5 years;
20 (29.8%) aged 6–9 years;
4 (6.0%) aged 10–13 years
30 (44.8%) have fair hair;
37 (55.2%) have dark hair
38 (56.7%) have short hair;
29 (43.3%) have long hair State of infestation at beginning of study: Medium-High (>20%).

Results

Out of the 62 participants of the test group, one child was infested (1.6%). Out of the 67 participants of the control group, 16 children were infested (23.8%). The calculated protection factor value was: (23.8/1.6)=14.9, indicating that the product gave excellent protection.

Since out of the test group only one child was infested, the analysis according to sectors of participants was statistically meaningless. During the course of the study no internal or external side effects were noted in the treated children. The status of the children was followed for a period of three months from the beginning of the study. During this period, no complaints of irritations, allergic reactions, photo-sensitivity or any other irregular occurrences were received. From studying the product components and as per the above mentioned follow-up, no health problem is expected from applying the product.

Modifications and variations of the present invention, a method and compositions for preventing lice infestation, will be obvious to those skilled in the art from the foregoing detailed description. Such modifications and variations are intended to come within the scope of the appended claims.

We claim:

1. A method to repel lice, comprising applying to a human or an animal susceptible to lice infestation an effective amount to repel but not kill lice of a terpenoid or a mixture of terpenoids in an acceptable carrier for topical application to a human or an animal, wherein the terpenoid is selected from the group consisting of a terpene-ol other than linalool, terpene ester, essential oil containing at least 40% terpene-ol or terpene-ester, cytral, nerol, ionone, dihydrocarvone, and pullegone, wherein the composition does not contain any non-terpenoid insecticides or repellants.

2. The method of claim 1, wherein the carrier comprises a terpenoid or mixture of terpenoids in a concentration of approximately between 0.01% and 10%.

3. The method of claim 1, wherein the terpenoid is selected from the group consisting of terpene-ols and terpene-esters, not including linalool.

4. The method of claim 1, wherein the carrier comprises an oil containing greater than 40% terpenoid by weight.

5. The method of claim 4, wherein the oil is a perfume.

6. The method of claim 1, wherein the terpenoid is an unsaturated terpene.

7. The method of claim 6, wherein the unsaturated terpenoid is selected from the group consisting of terpinene, pinene, limonene, myrcene, and carene.

8. The method of claim 3, wherein the terpene-ol is selected from the group consisting of perillyl alcohol, carveol, myrtenol, cis-verbenol, myrtanol, isopinocampheol, dihydrocarveol, isopulegol, terpineol, terpinen-4-ol, nerol, geraniol, menthol, $\beta$-citronellol, and dihydromyrcenol.

9. The method of claim 3, wherein the terpene-ester is selected from the group consisting of carvyl acetate, carvyl propionate, menthyl lactate, and iso bornyl acetate.

10. The method of claim 1, wherein the terpenoid contains an aldehyde functional group.

11. The method of claim 10, wherein the terpenoid aldehyde is selected from the group consisting of cytral and neral.

12. The method of claim 1, wherein the carrier is a material selected from the group consisting of an aqueous solution, an alcohol solution, a gel, a cream, a powder, spray, shampoo, conditioner, and hair styling mousse.

13. The method of claim 1, wherein the carrier further comprises a compound selected from the group consisting of antimicrobial preservatives, antioxidants, repellents for insects other than lice, fragrances, substances increasing binding of terpenes to hair, and substances delaying dissolution of the terpenes.

14. The method of claim 1, wherein the terpenoid is selected from the group consisting of essential oils containing at least 40% terpene-ol or terpene ester, further comprising a fragrance other than the terpene-ol or essential oil containing terpene-ol or terpene ester.

15. A method to repel lice, comprising applying to a human or an animal susceptible to lice infestation an effective amount to repel but not kill lice of a composition comprising linalool, essential oil containing at least 40% terpene-ol or terpene ester, and a terpene aldehyde in a topical carrier.

* * * * *